United States Patent [19]

Crivello

[11] Patent Number: 5,012,001
[45] Date of Patent: Apr. 30, 1991

[54] TRIARYL SULFONIUM PHOTOINITIATORS

[75] Inventor: James V. Crivello, Clifton Park, N.Y.

[73] Assignee: General Electric Company, Schenectady, N.Y.

[21] Appl. No.: 516,842

[22] Filed: Apr. 30, 1990

Related U.S. Application Data

[62] Division of Ser. No. 771,744, Sep. 3, 1985, abandoned.

[51] Int. Cl.$^5$ .......................... C07F 9/02; C07F 5/02; C07C 317/10; C07C 321/30
[52] U.S. Cl. .......................................... 568/13; 568/36; 568/57; 568/1; 568/2; 568/3; 568/6
[58] Field of Search ....................... 568/57 S, 13, 1, 2, 568/3, 6, 36 O–36 S

[56] References Cited

U.S. PATENT DOCUMENTS 3,321,403  5/1967  Campbell et al. ................ 568/57 X
4,173,476  11/1979  Smith et al. ....................... 528/90 X

OTHER PUBLICATIONS

Chemical Abstracts Service, Abstract No. 105:190652 (of DE 3537401 which is based on USSN 06/663643 (parent of this case)).

Primary Examiner—Frederick E. Waddell
Assistant Examiner—Catherine S. Kilby Scalzo
Attorney, Agent, or Firm—William A. Teoli; James C. Davis, Jr.; William H. Pittman

[57] ABSTRACT

Triarylsulfonium polyfluoro metal or metalloid salts are provided by effecting the oxidation of a diarylsulfide, while under dehydrating conditions, in the presence of a strong protonic acid. The resulting triarylsulfonium acid salt can thereafter be directly metathesized with an alkali metal or alkaline earth metal polyhalo salt.

These compounds have the general formula

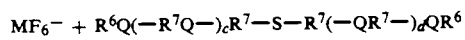

where Q is selected from =S→O, —S— and mixtures thereof, M is a transition metal or metalloid, "c" is an integer of 1 to 3, "d" is an integer of 0 to 3, $R^6$ is phenyl or naphthyl, $R^7$ is phenylene or naphthalene optionally substituted with one or more radicals selected from the class consisting of —$CH_3$, —$OCH_3$, —$CO_2H$, —Br, —Cl, and $NO_2$.

7 Claims, No Drawings

TRIARYL SULFONIUM PHOTOINITIATORS

This application is a division of application Ser. No. 771,744, filed Sept. 3, 1985, now abandoned.

BACKGROUND OF THE INVENTION

Reference is made to my copending application Ser. No. 663,643, filed Oct. 22, 1984.

Prior to the present invention, various methods were available for making the triphenylsulfonium chloride having the formula

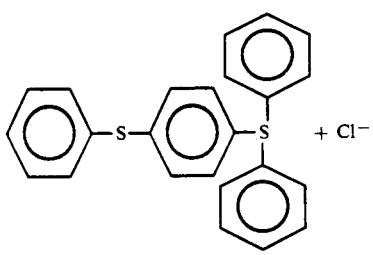
(1)

which thereafter could be metathesized with an alkali, or alkaline earth metal of a polyhalo metal or a metalloid salt. Some of these alkali or alkaline earth metal halo salts are preferably included within the formula $$MYX_n \quad (2)$$

where M is hydrogen or an alkali metal, for example, sodium, potassium or lithium, or an alkaline earth metal such as magnesium, barium, zinc, etc., Y is a metal or metalloid, for example, boron, phosphorous, antimony or arsenic, X is a halogen radical such as fluorine and n has a value of 4-6, inclusive.

One method is shown by Pitt, U.S. Pat. No. 2,807,648, using a direct Friedel Crafts condensation of an aromatic hydrocarbon employing aluminum chloride. Another procedure is shown by Crivello U.S. Pat. No. 4,374,066 assigned to the same assignee as the present invention employing diphenyl sulfide and aluminum chloride in combination with chlorine. Another procedure is shown by Smith U.S. Pat. No. 4,173,476 employing a mixture of diaryl sulfide and diarylsulfoxide in the presence of a strong acid. Although the aforementioned methods were useful for making the triarylsulfonium salts of formula (1), it was often found that the yields provided by the reaction were unsatisfactory or that the reactants such as diphenylsulfoxide rendered the method uneconomic. In addition, several of the aforementioned procedures required the isolation or separation of intermediates formed during the reaction before the desired end product was obtained. For example, the metathesis of the triarylsulfonium halide with an alkali metal or alkaline earth metal polyhalo metal or metalloid salt of formula (2), often requires the prior isolation of the triarylsulfonium halide.

The present invention is based on the discovery that polyarylsulfide, for example, compounds selected from $$RR^1S, \text{ and} \quad (3)$$

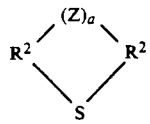
(4)

where R is selected from $C_{(6-14)}$ aryl radicals and substituted $C_{(6-14)}$ aryl radicals, $R^1$ is selected from R radi- $$RQR^3(-SR^4-)_b,$$

cals and $R^2$, $R^3$ and $R^4$ are selected from divalent $C_{(6-14)}$ arylene radicals, and substituted $C_{(6-14)}$ divalent arylene radicals, Q is selected from —O—, —S(O)—, —S— and mixtures thereof, Z is a member selected from —O—, —S— and —C($R^5$)$_2$—, $R^5$ is selected from hydrogen and $C_{(1-8)}$ monovalent organo radicals and a is a whole number equal to 0 or 1 and b is a whole number equal to 0 to 3 inclusive, can be partially oxidized to produce a fleeting mixture of diarylsulfide and diarylsulfoxide in situ, which thereafter, while in the presence of a dehydrating agent and a strong protonic acid, can be converted in situ, to the corresponding triarylsulfonium acid salt.

The triarylsulfonium acid salt can be directly metathesized without isolation with a polyhalo metal or metalloid salt of formula (2) to produce a triarylsulfonium polyhalo metal or metalloid salt in high yields.

STATEMENT OF THE INVENTION

There is provided by the present invention, a method for making triarylsulfonium polyhalo metal or metalloid salt utilizing polyarylsulfide of formulas (3) or (4) as a source material, which comprises, (A) effecting the metathesis of a triarylsulfonium acid salt with an alkali or alkaline earth metal salt of a polyhalo metal or metalloid to produce the corresponding metal or metalloid salt, (B) recovering the resulting triarylsulfonium polyhalo metal or metalloid salt from the mixture of (A), where the triarylsulfonium acid salt is the product produced by the partial oxidation of the polyarylsulfide source material which has been contacted under dehydrating conditions with a strong acid.

Some of the polyaryl sulfides which are included within formulas (3) and (4) are, for example,

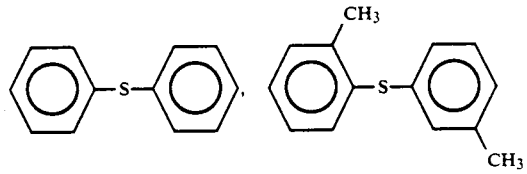

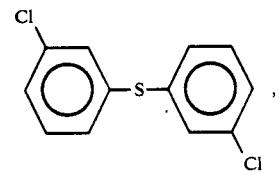

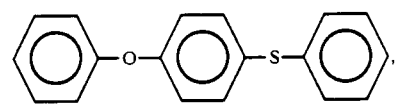

-continued

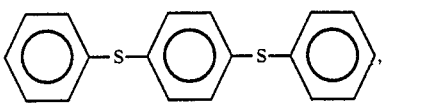

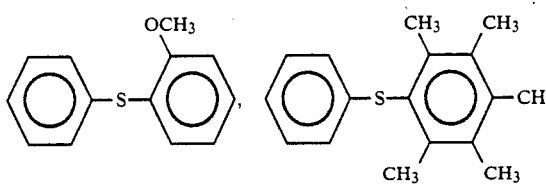

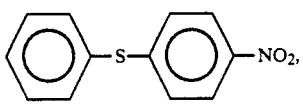

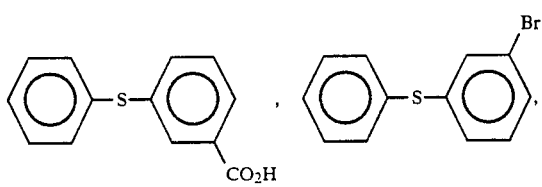

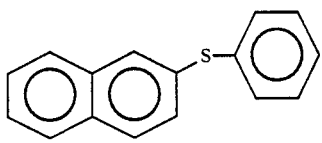

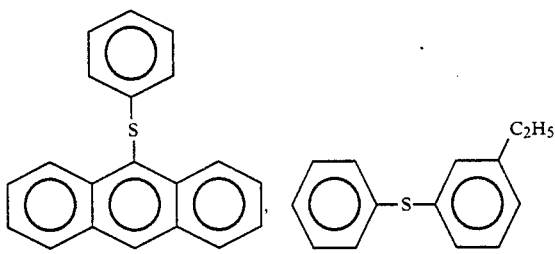

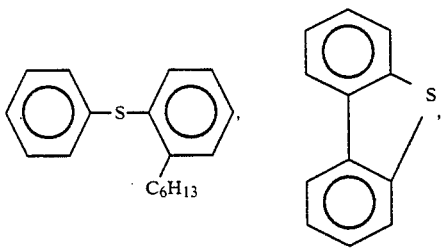

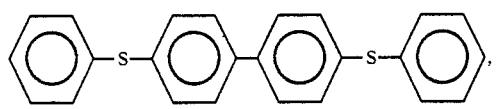

Radicals included with R and $R^1$ of formula (1) are, for example, phenyl, tolyl, xylyl, naphthyl, anthryl, chlorophenyl, methoxyphenyl; radicals included within $R^1$, $R^3$ and $R^4$ are, for example, phenylene, tolylene, xylylene, biphenylene, etc.

In addition to the use of the above described polyarylsulfides of formulas (3) and (4), there can be used polyarylene sulfide oligomers such as

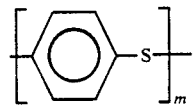

which can be prepared by the condensation of an alkali metal sulfide, such as sodium sulfide with a dihaloaromatic compound such as p-dichlorobenzene or p-dibromobenzene where m is an integer having a value of 1 to 8 inclusive. These polyarylene sulfide oligomers can be further arylated to give triarylsulfonium salts with either aryldiazonium salts or diaryliodonium salts in the presence of a copper salt catalyst such as copper benzoate and a strong acid. Alternatively, they may be partially oxidized and condensed to give polytriarylsulfonium salts.

Among the oxidizing agents which can be utilized in the practice of the present invention are, for example, $CH_3CO_3H$, $HCO_3H$, $CH_3CH_2CO_3H$, $C_6H_5CO_3H$, m—Cl—$C_6H_4CO_3H$, $H_2O_2$, iodosobenzene, iodosobenzene diacetate, potassium persulfate, sodium periodate, t-butyl hypochlorite, bromine, chloramine-B and chlorobenzotriazole.

Some of the dehydrating agents which can be used in the practice of the invention include, for example, acetic anhydride, phosphorous pentoxide, polyphosphoric acid, maleic anhydride, phthalic anhydride, sulfur dioxide, trifluoroacetic anhydride and concentrated sulfuric acid.

The term "strong acid" used in the description of the present invention means sulfuric acid, perchloric acid, nitric acid, fluoroboric acid, hydrofluoric acid and benzene sulfonic acid.

Among the polyhalo metal or metalloid salts of formula (2) there are included $NaAsF_6$, $KPF_6$, $NaSbF_6$, $NaBF_4$, $KsbCl_6$, $NaFeCl_4$, $Li_2BiCl_5$, $NaSnCl_6$ and $HAsF_6$. Additional compounds which can be used to metathesize the triarylsulfonium acid salt made by the practice of the invention are, for example, $KClO_4$, $NaCO_2CF_3$, $KSO_3CF_3$, $KSO_3C_6H_5$, In the practice of the present invention, the diarylsulfide is partially oxidized, utilizing an oxidizing agent as previously defined. In order to provide for effective results, it has been found that a mixture of about 0.2 to 0.7 moles of oxidizing agent, per mole of sulfide within the molecule can be used. The reaction can be facilitated by the employment of an organic solvent if desired. Some of the organic solvents which can be used are, for example, chloroform, methylene chloride, carbon tetrachloride, acetic acid, benzene, chlorobenzene.

Temperatures in the range of from 0 to 90° C. will provide for satisfactory results with respect to the partial oxidation of the diarylsulfide.

In order to provide for the conversion of the resulting mixture of diarylsulfide and diarylsulfoxide sufficient dehydrating agent and strong acid can be utilized. In instances where concentrated sulfuric acid is used, it can serve as both a strong acid and dehydrating agent. Temperatures which can be employed to effect the partial oxidation of the diarylsulfide along with dehydration and protonation are, for example, from 0° C. to 100° C. and preferably from 0° C. to 60° C.

Upon completion of the conversion of the diarylsulfide to the mixture of diarylsulfide and diarylsulfoxide which can be effected within 1 to 10 hours within the aforementioned operating conditions, the dehydration and protonation of resulting components to the corresponding triarylsulfonium acid salt can be effected. Thereafter, the metathesis reaction can be achieved by adding a solution of the polyhalo metalloid or metal salt to the reaction mixture, or pouring it directly into an aqueous solution of the polyhalo metal or metalloid salt which has been chilled depending upon the particular conditions. Recovery of the desired triarylsulfonium hexafluoro metalloid salt can then be effected utilizing standard recovery procedures such as recrystallization, filtration, etc.

The following examples are given by way of illustration and not by way of limitation. All parts are by weight.

EXAMPLE 1

There is slowly added with stirring 4.75 grams (0.025 mole) of 40% peracetic acid to a mixture cooled to 0° C, consisting of 9.3 grams (0.05 mole) of phenylsulfide, 12.5 ml. acetic anhydride and 30 ml. of methylene chloride. The mixture was stirred and a slight exothermic reaction was noted. Upon completion of the addition, there was added 1.5 ml. of concentrated sulfuric acid which was added slowly while maintaining the temperature below 10° C. The color of the reaction mixture became initially light purple and then gradually faded upon standing. After 1 hour at room temperature, there was added to the mixture, 5.7 grams potassium hexafluoroarsenate which was dissolved in approximately 50 ml. distilled water. The mixture was vigorously stirred for 1.5 hours and then the methylene chloride layer was separated using a separatory funnel. The methylene chloride was then removed using a rotary evaporator leaving a yellow oil. A white crystalline product was obtained by treating the yellow oil with ether. Recrystallization from methanol gave a product having a melting point of 86-88° C. Based on method of preparation, the product was diphenyl-4-thiophenoxyphenylsulfonium hexafluoroarsenate. The identity of the product was further confirmed by its NMR spectrum. The yield of the recrystallized product was 3.2 grams or a 23% yield.

A solution containing 3% by weight of the above photoinitiator was evaluated as a photoinitiator in 4-vinylcyclohexene oxide. The resulting solution was drawn as a 3 mil film on a glass plate and irradiated using a GE H3T7 medium pressure mercury arc lamp. A tack-free film was obtained in less than 1 second.

EXAMPLE 2

The procedure of Example 1 was repeated except that in place of the potassium hexafluoroarsenate there was employed 4.6 grams of potassium hexafluorophosphate. There was obtained 5.6 grams or a 43.4% yield of diphenyl-4-thiophenoxyphenylsulfonium hexafluorophosphate having a melting point of 91-93° C. after recrystallization from methanol. The aforementioned sulfonium hexafluorophosphate salt also provided a tack-free time of 1 second when a 3% solution of the photoinitiator dissolved in 4-vinylcyclohexene dioxide was evaluated as a 3 mil film on glass.

EXAMPLE 3

There was added at 0° C. in a dropwise manner, 4.75 grams (0.025 mole) of 40% peracetic acid solution to a mixture while it was stirring of 9.3 grams (0.05 mole) of phenylsulfide, 12 ml. of acetic anhydride, 30 ml. of methylene chloride and 1.5 ml. of concentrated sulfuric acid. The temperature of the mixture was maintained below 10° C. for 1 hour with continuous stirring. There was then added 5.7 grams of potassium hexafluoroarsenate dissolved in 50 ml. of water and the reaction mixture worked up as described in Example 1. There was obtained a yield of 6.65 grams (47.5%) of diphenyl-4-thiophenoxyphenylsulfonium hexafluoroarsenate after it was recrystallized from methanol.

EXAMPLE 4

A mixture of 9.3 grams (0.05 mole) of phenylsulfide and 6.75 grams (0.025 mole) of potassium persulfate was stirred while 25 ml. of cooled concentrated sulfuric acid was added dropwise while maintaining the temperature at 0-5° C. A deep purple color developed in the solution which slowly changed to green. The mixture was allowed to stir at room temperature for 1 hour. The mixture was then poured into 100 ml. of ice water containing 5.7 grams of potassium hexafluoroarsenate. A white precipitate was obtained. Based on method of preparation the product was diphenyl-4thiophenoxyphenylsulfonium hexafluoroarsenate. Its identity was further confirmed by its melting point and its NMR spectrum. The yield of product was 8.8 grams which was 63% of the theoretical. A tack-free time of 1 second was obtained when a 3% solution of the hexafluoroarsenate sulfonium salt was evaluated as a photoinitiator in 4-vinylcyclohexene dioxide and exposed as a 3 mil film on glass to a GE H3T7 lamp.

EXAMPLE 5

There was added 1.5 ml. of concentrated sulfuric acid to a mixture of 9.3 grams (0.05 mole) of phenylsulfide, 12.5 ml. of acetic anhydride and 4.75 grams (0.025 mole) of 40% peracetic acid which was maintained at 0° C. The resulting mixture was stirred for 1 hour and then the mixture was poured into a solution of 5.7 grams of potassium hexafluoroarsenate dissolved in 100 ml. of water. The resulting product was a pale yellow oil which was recrystallized from methanol. Based on method of preparation, the product was diphenyl-4-thiophenoxyphenylsulfonium hexafluoroarsenate. It was obtained in the yield of 30.4%. It was found to be an effective photoinitiator when evaluated as shown in Example 4.

EXAMPLE 6

The procedure of Example 5 was repeated except that there was utilized 6.5 grams of sodium hexafluoroantimonate in place of the 5.7 grams of potassium hexafluoroarsenate. There was obtained a 39% yield of diphenyl-4thiophenoxyphenylsulfonium hexafluoroantimonate. A tackfree time of approximately 0.5 seconds was obtained when a 3% solution of the hexafluoroantimonate salt was evaluated as a photoinitiator in 4-vinylcyclohexene dioxide in accordance with the procedure of Example 4.

EXAMPLE 7

There was added dropwise 4.75 grams (0.025 mole) of a 40% peracetic acid solution to a mixture of 14.7 grams (0.5 mole) of 1,4-dithiophenoxybenzene, 20 ml. of acetic acid and 15 ml. of methylene chloride which was being stirred. The addition of the peracetic acid was conducted at a rate sufficient to maintain the reaction at about 15° C. An orange colored reaction mixture was obtained which became homogeneous. After 0.5 hour of stirring at room temperature, the reaction mixture was cooled to 10° C. and 15 ml. of acetic acid was added. There was added to the resulting solution in a dropwise manner, 5 ml. of concentrated sulfuric acid. A deep purple color was observed as the acid was added which slowly faded to yellow when approximately half of the sulfuric acid had been added. At the completion of the addition, the reaction mixture was allowed to stir for 2 hours. The solution was then poured into 300 ml. of cold water and 5 grams of $KPF_6$ in 50 ml. of water was added. The resulting solution was stirred for 1 hour. The methylene chloride layer was separated from the aqueous layer by means of a separatory funnel and the solvent was evaporated using a rotary evaporator. An oil was obtained which was purified by chromatographing it on neutral alumina using methylene chloride as an eluent. The product was washed with cyclohexane and the solidified glassy product was obtained in approximately a 50% yield and had a long melting point starting at around 62° C. Based on method of preparation and elemental analysis, the product had the following formula

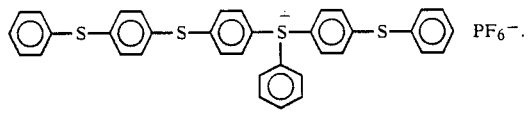

Calculated for $C_{36}H_{27}S_6PF_6$: %C, 59.02; %H, 3.69; %P, 4.23. Found: %C, 58.69; %H, 3.94; %P, 4.05.

A mixture of 4-vinylcyclohexene dioxide and 3% by weight of the above photoinitiator was applied onto an aluminum substrate. The coated substrate was found to provide a tack-free film in less than 1 second when exposed to ultraviolet light using an H3T7 lamp at a distance of 4 inches.

EXAMPLE 8

The above procedure was repeated, except that after the oxidation step of the 1,4-dithiophenoxybenzene there was used 5 ml. of acetic acid and 10 ml. of concentrated sulfuric acid. The resulting mixture was then divided into two equal parts. One of the parts was metathesized with sodium hexafluoroantimonate. There was obtained a 75.8% yield of an off-white solid having a melting point of about 82° C. Based on method of preparation, the product had the following formula

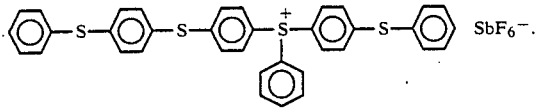

Calculated %C, 52.49; %H, 3.28; %S, 15.55. Found: %C, 52.19; %H, 3.59; %S, 15.77.

There was added to the other half of the mixture potassium hexafluoroarsenate. The solution was triturated in n-hexane and the resulting oil further washed several times with more n-hexane. There was obtained an off-white glassy product which on vacuum drying provided a 75.8% yield of product. Based on method of preparation, the product was a photoinitiator having the following formula:

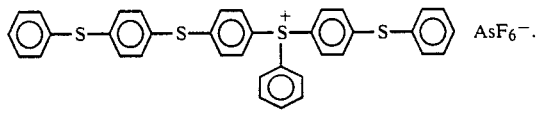

Calculated: %C, 55.64; %H, 3.48; %S, 16.49. Found: %C, 54.61; %H, 3.70; %S, 16.47.

EXAMPLE 9

There was added 9.5 grams (0.05 mole) of 35% peracetic acid to a mixture which was being stirred of 18.42 grams (0.1 mole) of dibenzothiophene, 30 ml. of acetic acid and 10 ml. of methylene chloride. During the addition, a mild exotherm was noted with the temperature rising to 30° C. The reaction mixture was stirred at room temperature for 1 hour following the addition of the peracetic acid. There was then added to the mixture, 30 ml. of acetic anhydride followed by the dropwise addition of 10 ml. of concentrated sulfuric acid. The reaction mixture was cooled during the addition to maintain the temperature below 15° C. Additional 5 ml. of methylene chloride was added to alleviate the caking in the flask and the mixture was stirred for one hour and then poured into approximately 300 ml. of water containing 0.05 mole of potassium hexafluorophosphate. A tan precipitate was obtained which was recovered by filtration and washed with water followed with ethylether. The resulting product was dried in vacuo over a period of about 12 hours at 60° C. There was obtained 19.7 grams or an 82% yield of product. Based on method of preparation the product had the following formula,

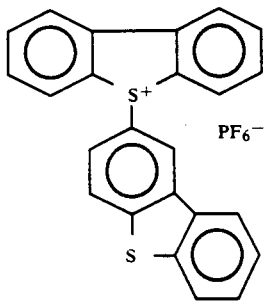

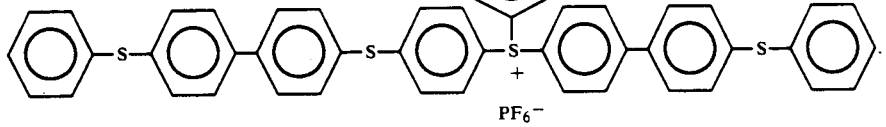

A 3% solution of the above photoinitiator was prepared by dissolving the salt in 4-vinylcyclohexene dioxide. The resulting mixture was spread as a 1 ml. film on a glass plate and irradiated using a GE H3T7 medium pressure mercury arc lamp. A tack-free cure was obtained within 2-3 seconds.

EXAMPLE 10

There was added 19.6 grams (0.34 mole) of powered potassium hydroxide to a solution of 33.0 g (0.3 mole) of thiophenol in 120 ml. of dimethylacetamide. The temperature of the reaction mixture spontaneously rose to 50° C. After the exotherm had subsided, the reaction mixture was heated to 165° C. until 20 ml. of water was collected over a period of about 1 hour. There was then added to the cooled solution, 44.8 grams (0.15 mole) of 4,4'-dibromobiphenyl. After the addition, the solution was heated to reflux for 6 hours. After the mixture had cooled, there was added approximately 300 ml. of water to produce a slightly tan precipitate which was collected by suction filtration, washed with water and dried for about 12 hours at 60° C. in vacuo. The yield of product was quantitative. Based on method of preparation the product was a bisulfide having the formula,

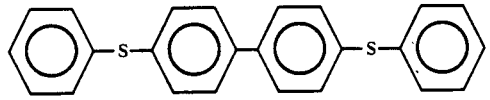

There was added dropwise, 4.75 grams (0.025 mole) 40% peracetic acid to a mixture of 18.5 grams (0.05 mole) of the above bisulfide, 20 ml. of glacial acetic acid and 40 ml. of methylene chloride. The addition of the peracetic acid was controlled to maintain the temperature at 10-15° C. After the reaction had been completed, the reaction mixture was stirred at 25° for 1.5 hours. The reaction mixture was then cooled again to 10° C. and 15 ml. of acetic anhydride was added dropwise followed by 5 ml. of concentrated sulfuric acid. During the addition, the temperature was maintained at 10-15° C. and then stirred at room temperature for 2 hours. The reaction mixture was poured into 300 ml. of water and 5 grams of potassium hexafluorophosphate was added suspended in 100 ml. of methylene chloride. The mixture was stirred for 12 hours and then sodium chloride was added to saturate the aqueous layer. The methylene chloride layer was retained and the solvent removed leaving a solid which was washed with ethylether. There was obtained a product which was purified by recrystallization from acetonitrile. Based on method of preparation, the product was a arylsulfonium salt having the formula

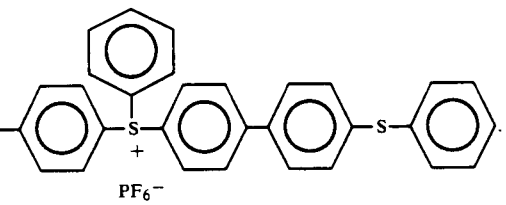

A 3% solution of the above sulfonium salt in 4-vinylcyclohexene dioxide was spread as a one-mil film onto a glass plate and irradiated at a distance of approximately 6 inches from a GE H3T7 medium pressure mercury arc lamp. A tack-free film was obtained after an irradiation period of 5 seconds.

EXAMPLE 11

There was added dropwise 19.0 grams (0.10 mole) of 40% peracetic acid to a mixture of 20.1 grams (0.05 mole) of di-4,4'-thiophenoxyphenylsulfide, 40 ml. of acetic acid and 20 ml. of methylene chloride. The addition of the peracetic acid was maintained at such a rate that the reaction temperature did not exceed 10-15° C. The reaction mixture was allowed to stir for 1 hour after the addition had been completed and then it was poured into 300 ml. of water. The methylene chloride layer was separated and the solvent removed using a rotary evaporator. A yellow oil was obtained which was purified by recrystallization from acetonitrile-ethylether. Based on method of preparation, the product was a trissulfoxide having the formula,

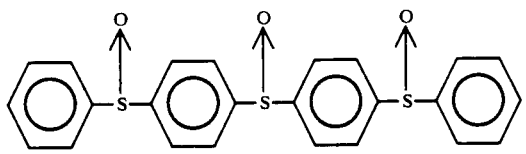

Calculated: C, 64.0; %H, 4.0; %O, 10.66. Found: %C, 64.13; %H, 3.99; %O, 10.39.

There was added dropwise 5 ml. of concentrated sulfuric acid to a mixture of 3.5 grams (0.008 mole) of the above trissulfoxide, 10 ml. of acetic anhydride and 5 grams of phenylsulfide. Addition of the sulfuric acid was maintained at a rate which allowed for a temperature not exceeding 10-15° C. After the addition was complete, the reaction mixture was stirred at room temperature for 2 hours and then poured into 300 ml. of water containing 4.0 gram of potassium hexafluorophosphate and 20 ml. of methylene chloride. The methylene chloride layer was separated and the solvent evaporated. There was obtained a white solid which was washed with ethylether, filtered and dried in vacuo at 60° C. Crystallization from acetonitrile/ethylether, provided a product. Based on method of preparation and its IR spectra, the product was a arylsulfonium hexafluorophosphate salt having the formula

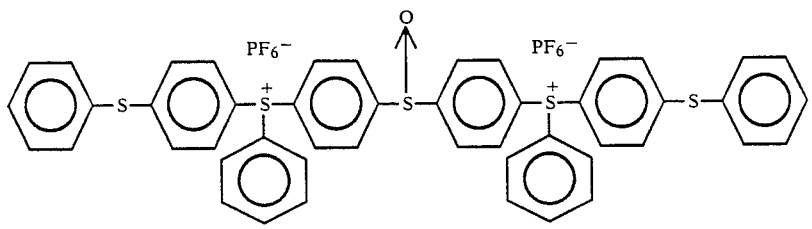

The above bis-sulfonium salt was dissolved in 4-vinylcyclohexene dioxide to provide a 3% solution. A 1 mil film of the above solution was UV cured as described in Example 10. The film was tack-free after an irradiation period of 1 second.

Although the above examples are directed to only a few of the very many variables which can be utilized in the practice of the present invention, it should be understood that the present invention is directed to the use of a much broader variety of diarylsulfides, oxidizing agents, acids and dehydrating agents as shown in the description preceding these examples. In addition, the following aryl sulfonium salts are also provided:

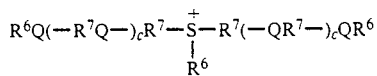

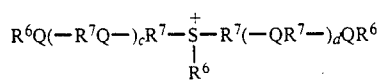

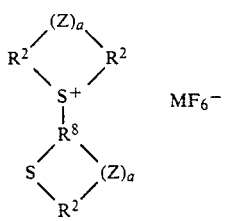

where $R^6$ is selected from $C_{(6-14)}$ aryl radicals and substituted $C_{(6-14)}$ aryl radicals, $R^7$ is selected from divalent $C_{(6-14)}$ arylene radicals and substituted $C_{(6-14)}$ arylene radicals, Q is selected from —O—, —S(O)—, —S— and mixtures thereof, M is a transition metal or a metalloid, $R^2$ is a divalent arylene radical selected from $R^6$ radicals, $R^8$ is a trivalent $C_{(6-14)}$ arylene radical or substituted $C_{(6-14)}$ arylene radical, Z is selected from —O—, —S— and —C($R^5$)$_2$, $R^5$ is selected from hydrogen and $C_{(1-8)}$ monovalent radicals, a is a whole number equal to 0 or 1, c is an integer equal to 1 to 3 and d is a whole number equal to 0 to 3 inclusive.

In addition to the above arylsulfonium salts, there is also included in the present invention, sulfonium salts having the following formula

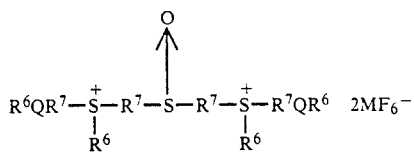

where $R^6$, $R^7$ and Q are defined above.

What is claimed is:

1. Arylsulfonium salts having the formula

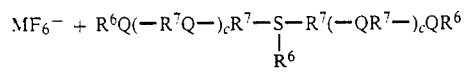

where $R^6$ is phenyl or naphthyl, $R^7$ is an aromatic radical selected from phenylene or naphthylene or an aromatic radical selected from phenylene or naphthylene substituted with one or more radicals selected from the class consisting of —CH$_3$, —OCH$_3$, —CO$_2$H, —Br, —Cl and NO$_2$, Q is selected from =S→O, —S— and mixtures thereof, M is a transition metal or a metalloid, and c is an integer equal to 1 to 3 inclusive.

2. Aryl sulfonium salts having the formula,

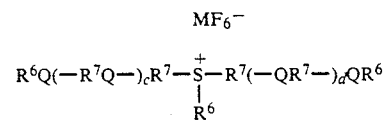

where $R^6$ is phenyl or naphthyl, $R^7$ is an aromatic radical selected from phenylene or naphthylene or an aromatic radical selected from phenylene or naphthylene substituted with one or more radicals selected from the class consisting of —CH₃, —OCH₃, —CO₂H, —Br, —Cl and NO₂, Q is selected from =S→O, —S— and mixtures thereof, M is a transition metal or a metalloid, and c is an integer equal to 1 to 3 inclusive and d is a whole number equal to 0 to 3 inclusive.

3. Aryl sulfonium salts having the formula,

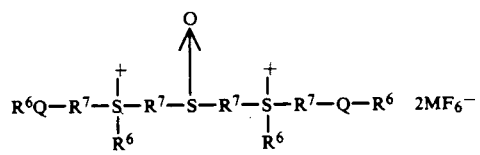

where R⁶ is phenyl or naphthyl, R⁷ is an aromatic radical selected from phenylene or naphthylene or an aromatic radical selected from phenylene or naphthylene substituted with one or more radicals selected from the class consisting of —CH₃, —OCH₃, —CO₂H, —Br, —Cl and NO₂, Q is selected from =S→O, —S— and mixtures thereof, M is a transition metal or a metalloid.

4. The compound

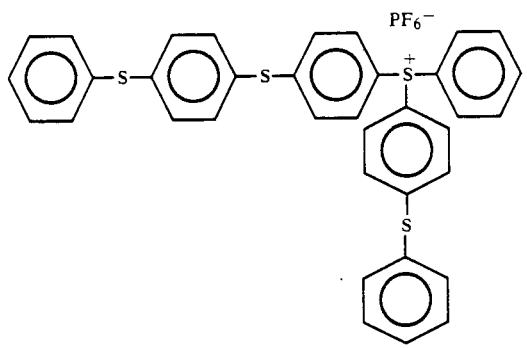

5. The compound

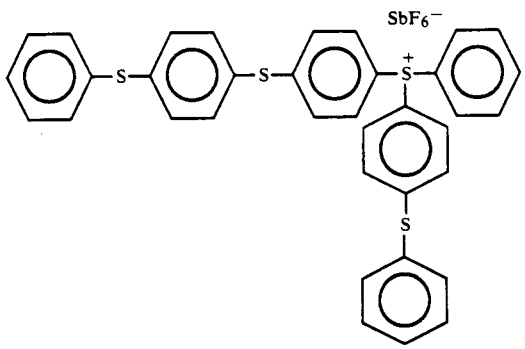

6. The compound

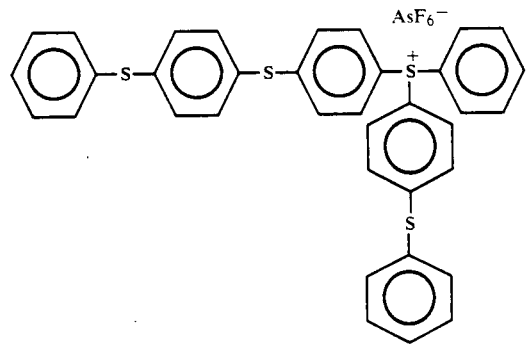

7. The compound

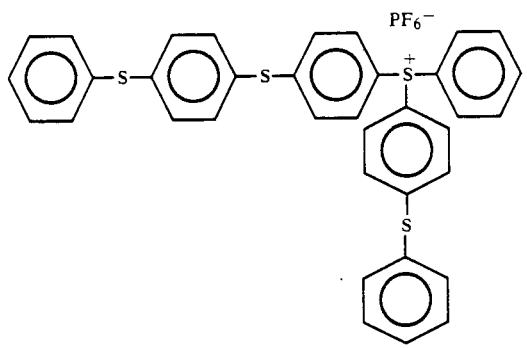

* * * * *